United States Patent [19]

Chen et al.

[11] Patent Number: 5,575,790
[45] Date of Patent: Nov. 19, 1996

[54] SHAPE MEMORY ALLOY INTERNAL LINEAR ACTUATOR FOR USE IN ORTHOPEDIC CORRECTION

[75] Inventors: Michael M. Chen, Troy; Robert S. Hirsch, New York; James A. Fairweather, East Nassau; Andrew B. Wright, Latham; Kevin C. Craig, Corinth; Allen Carl, Slingerland, all of N.Y.

[73] Assignee: Rensselaer Polytechnic Institute, Troy, N.Y.

[21] Appl. No.: 440,304

[22] Filed: Mar. 28, 1995

[51] Int. Cl.$^6$ .................................................. A61B 17/68
[52] U.S. Cl. ............................ 606/60; 606/61; 606/78; 192/45
[58] Field of Search ..................... 606/61, 78, 63, 606/68, 72, 60, 57, 58, 54, 105; 310/96, 100; 192/45, 38, 82 T, 89.2, 92

[56] References Cited

U.S. PATENT DOCUMENTS

| | | |
|---|---|---|
| 4,641,636 | 2/1987 | Cotrel . |
| 4,854,304 | 8/1989 | Zielke . |
| 5,010,897 | 4/1991 | Leveen . |
| 5,074,882 | 12/1991 | Grammont et al. ............... 606/63 |
| 5,147,360 | 9/1992 | Dubousset . |
| 5,415,660 | 5/1995 | Campbell et al. .................. 606/68 |
| 5,505,733 | 4/1996 | Justin et al. ...................... 606/63 |

FOREIGN PATENT DOCUMENTS

| | | | |
|---|---|---|---|
| 4009626 | 11/1991 | Germany ......................... 192/82 |
| 8802462 | 5/1990 | Netherlands ..................... 606/57 |
| 8707134 | 12/1987 | WIPO ............................... 606/61 |

*Primary Examiner*—Guy V. Tucker
*Assistant Examiner*—Julian W. Woo
*Attorney, Agent, or Firm*—Nixon & Vanderhye P.C.

[57] ABSTRACT

An implantable linear actuator device for use in orthopedic correction procedures, the device comprising a housing including a first tubular portion and a second tubular portion, the second tubular portion slidably received in telescoping relationship within the first tubular portion; and a drive mechanism secured within the housing and connected between the first and second tubular portions, the drive mechanism including a main screw shaft rotatably journalled at one end in the first tubular portion and threadably connected at an opposite end to the second tubular portion; a one-way rotatable clutch engageable with the main screw shaft such that rotation of the clutch in one direction will effect rotation of the main screw shaft in the one direction but rotation of the clutch in an opposite direction will not rotate the main screw shaft; and a shape memory alloy component fixed between the clutch and the first tubular portion such that, upon application of heat, the component causes the clutch and the screw shaft to rotate in the one direction.

13 Claims, 5 Drawing Sheets

FIG. 12
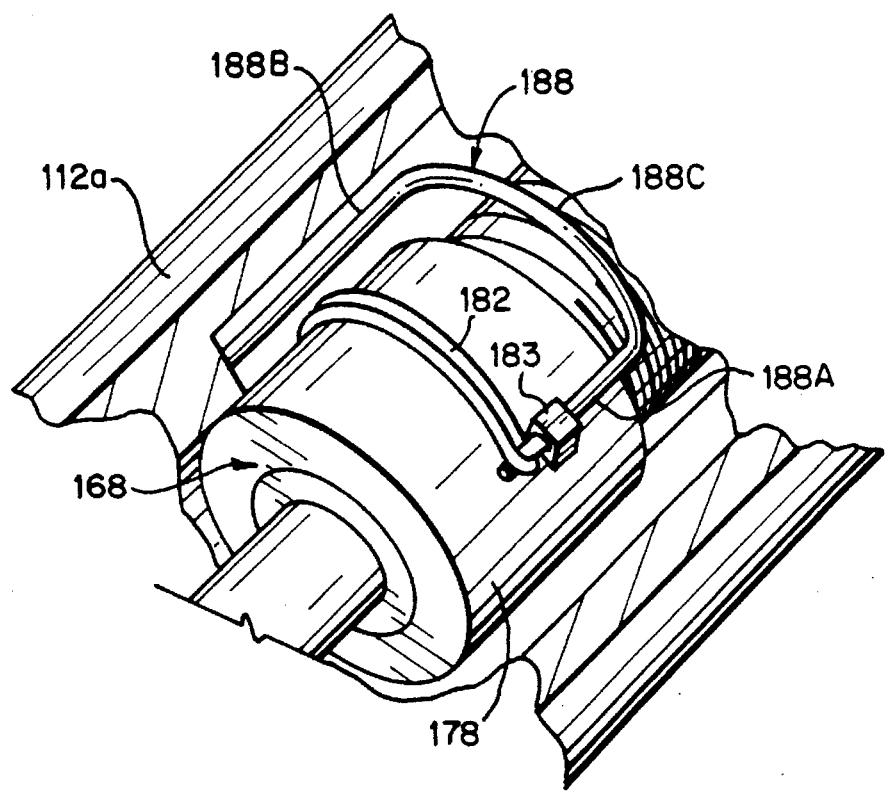
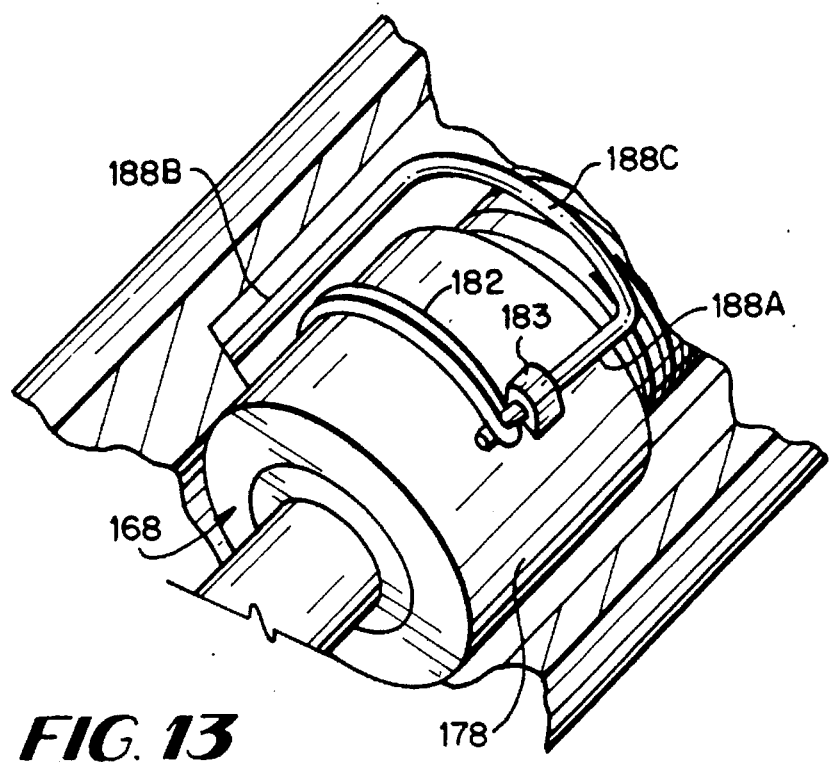
FIG. 13

SHAPE MEMORY ALLOY INTERNAL LINEAR ACTUATOR FOR USE IN ORTHOPEDIC CORRECTION

This invention relates to an externally controllable linear actuator device which can be embedded within the body to exert corrective forces and moments on bone segments in the treatment of deformities, such as scoliosis or shortened limbs comminuted and complex fractures.

BACKGROUND OF THE INVENTION

Scoliosis is a lateral curvature of the spine which may be caused by, in effect, a buckling of the spinal column during an adolescent growth spurt. In addition to lateral curvature, the vertebrae are rotated with respect to each other. Once adulthood is reached, the spinal column stabilizes, unless the angle of the spine exceeds about 45 degrees.

The current treatment of severe scoliosis is by manually deforming the spinal column and attaching a correction device to the spine such as the Cotel-Dubousset system, as disclosed, for example, in U.S. Pat. No. 5,147,360. The problem with this kind of treatment is that a drastic change in spinal structure occurs over a relatively short period of time, and such change can traumatize the spinal cord resulting in paralysis of the patient.

There has been some efforts toward fixing Nitinol rods directly to the spine, and actuating the rods non-invasively, by high energy electromagnetic waves.

Studies in limb lengthening have shown that nerve tissue in the extremities will viscoelastically stretch if stressed gradually. Peripheral nerve cells cord and become larger. Based on these studies, it is postulated that the spinal column itself might also elongate or stretch if stressed in the same gradual fashion. Thus, the invention here relates to a device which can be fixed to bone by bone screws, and which can exert gradually over a period of time, precise linear increments on specific bone segments in order to either reorient these segments both or stretch them apart. The device itself is designed to be actuated and controlled by external commands, thus eliminating the currently employed direct manipulative procedures required to adjust currently available fixation systems.

The linear actuator in accordance with this invention includes a generally cylindrical, tubular housing which includes a first section and a second section (or expander sleeve) telescopically received within the first section. One end of the first housing section is closed by a threaded plug while one end of the second housing section is formed with an integral closed end. The housing rotationally supports a main drive screw which extends through open ends of the first and second sections and which is threadably received at one end within a nut fixed within the second housing section. The other end of the main screw is rotatably journalled in a bearing fixed within the first housing section. As a result, rotation of the screw results in linear or axial movement of the second housing section or expander sleeve out of the first housing section, thereby serving to axially lengthen the device as a whole.

Both the plug at the one end of the housing and the expander sleeve at the other end of the housing include mounting tabs for fixing the device to specific bone segments by bone screws or the like.

A clutch mechanism is mounted on the main drive screw within the housing and is preferably of a one-way, cammed roller type. In other words, rotation of the clutch in one direction causes rollers to grip the screw shaft and rotate the shaft in the same direction. Rotation in the opposite direction, however, results in a release of the clutch from the shaft so that the clutch can freely rotate without any rotational effect on the shaft. In accordance with this invention, a shape memory alloy component is fixed at circumferentially spaced locations (180° apart) between the housing and a clutch retainer ring, fixed about the clutch, and at the same time, a return spring is fixed at circumferentially opposed locations between the housing and the clutch retainer ring, and acting in the opposite direction. With this arrangement, when the shape memory alloy component is heated, it will contract causing the clutch and the main screw shaft to rotate in the first direction which will result in axial or linear movement of the second housing section or expander sleeve relative to the first housing section to thereby axially lengthen the device. When heat is removed, the shape memory alloy component softens, allowing the return spring to pull the clutch back in an opposite direction of rotation, but without effect on the screw shaft. In other words, removal of heat or cooling of the shape memory alloy component returns the clutch to its original position, but the device itself remains in its extended state. Subsequent heating steps at various intervals will serve to incrementally expand the device even further, in accordance with predetermined treatment procedures.

In an alternative arrangement, the shape memory alloy component is in the form of a generally J-shaped rod spring, one end of which is attached to the housing and the other end of which is attached to the clutch retainer ring. Operation is essentially the same as described above.

In the exemplary embodiment, external radio wave commands and high energy field waves may be utilized to actuate the device. The device will decode the radio waves and transform the electric-magnetic high energy waves to thermal energy which, in turn, will heat the shape memory alloy component.

Thus, in accordance with its broader aspects, the present invention relates to an implantable linear actuator device for use in orthopedic correction procedures, the device comprising a housing including a first tubular portion and a second tubular portion, the second tubular portion slidably received in telescoping relationship within the first tubular portion; and a drive mechanism secured within the housing and connected between the first and second tubular portions, the drive mechanism configured and arranged to convert rotational movement to linear movement to thereby extend the second tubular portion in a direction away from the first tubular portion; and externally actuatable shape memory alloy means connected to the drive mechanism for imparting rotational motion to the drive mechanism.

In another aspect, the invention relates to an implantable linear actuator device for use in orthopedic correction procedures, the device comprising a housing including a first tubular portion and a second tubular portion, the second tubular portion slidably received in telescoping relationship within the first tubular portion; and a drive mechanism secured within the housing and connected between the first and second tubular portions, the drive mechanism including a main screw shaft rotatably journalled at one end in the first tubular portion and threadably connected at an opposite end to the second tubular portion; a one-way rotatable clutch engageable with the main screw shaft such that rotation of the clutch in one direction will effect rotation of the main screw shaft in the one direction but rotation of the clutch in an opposite direction will not rotate the main screw shaft; and a shape memory alloy component fixed between the clutch and the first tubular portion such that, upon application of heat, the component causes the clutch and the screw shaft is to rotate in the one direction.

The device in accordance with this invention reduces the risk of paralysis or pain which might otherwise occur in a one-time surgical procedure. It also serves to allow incremental lengthening of shortened long bones and also allows for compression or distraction forces to enhance healing. It is small in size and provides precise linear displacement under variable loading.

Additional objects and advantages will become apparent from the detailed description which follows.

BRIEF DESCRIPTION OF THE DRAWINGS

FIG. 12 is a part perspective view, partially cut away, illustrating an alternative embodiment of the invention;

FIG. 13 is a view similar to FIG. 12, with the actuator in an extended state.

DETAILED DESCRIPTION OF THE DRAWINGS

Figure 1:
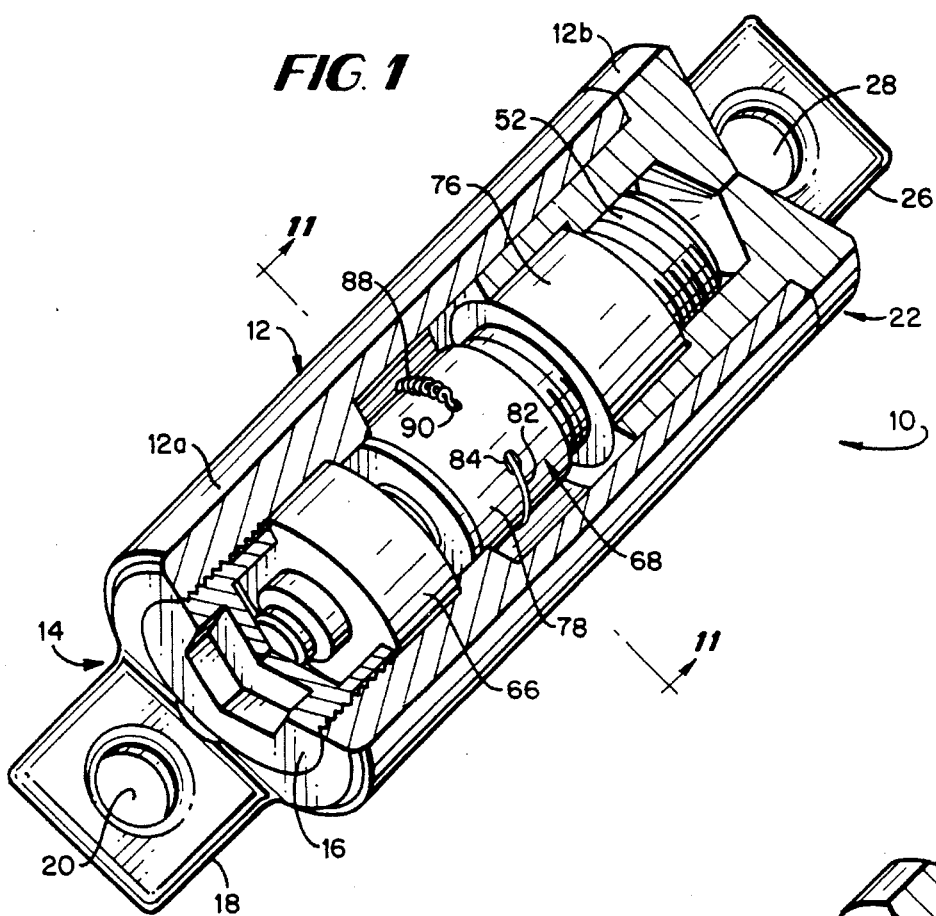
FIG. 1 is a perspective view, partially cut away, illustrating the shape memory alloy internal linear actuator in accordance with this invention.
Figure 2:
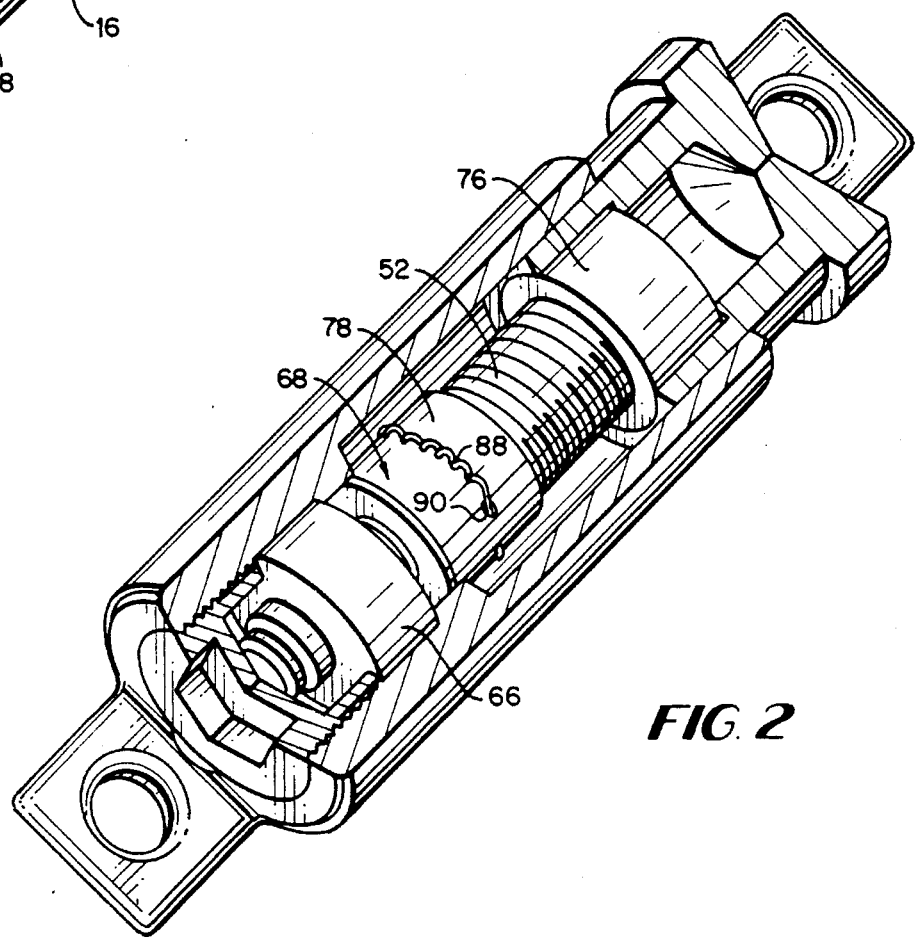
FIG. 2 is a perspective view, partially cut away, of the device shown in FIG. 1 but in an extended state.
Figure 4:
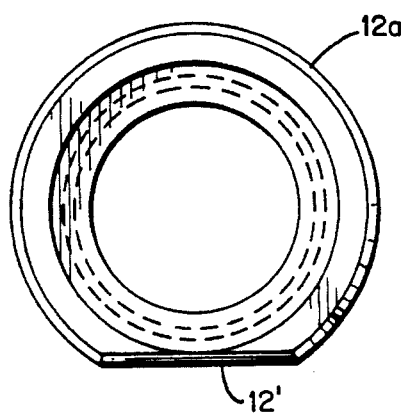
FIG. 4 is an end view of the housing section illustrated in FIG. 3.
Figure 5:
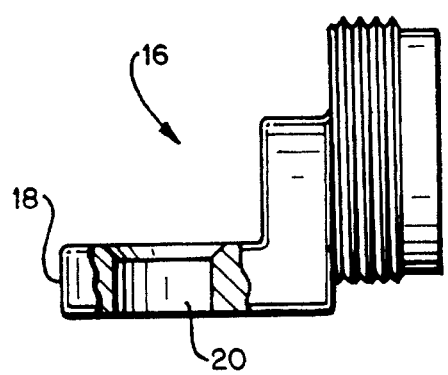
FIG. 5 is a side elevation, partly in section, illustrating a plug used to close one end of the first section of the housing.

Turning now to FIGS. 1 and 2, the shape memory alloy internal linear actuator 10 includes a generally cylindrical, tubular housing 12 including telescopingly connected housing sections 12a and 12b. At one end 14, the first housing section 12a is closed by a plug 16 threadably received within the housing. The plug 16 is formed with an attachment tab 18 (see FIG. 5) having a bone fixation hole 20 oriented so that the center axis of the hole extends perpendicularly to the longitudinal center axis of the actuator itself. The opposite end 22 of the housing section 12a slidably receives the second housing section, or expander sleeve, 12b which is also generally cylindrical in shape. The second housing 12b is formed with an attachment tab 26 which is similar to the tab 18, and also includes a bone fixation hole 28. From FIG. 4, it can be appreciated that the housing 12 has a flat surface 12' extending axially along the housing from one end to the other including both sections 12a and 12b, generally aligned with the generally planar attachment tabs 18 and 26. To gain an appreciation for the size of the device, the housing diameter is about 0.375" and the housing is less than 2 inches in length, when contracted.

Figure 3:
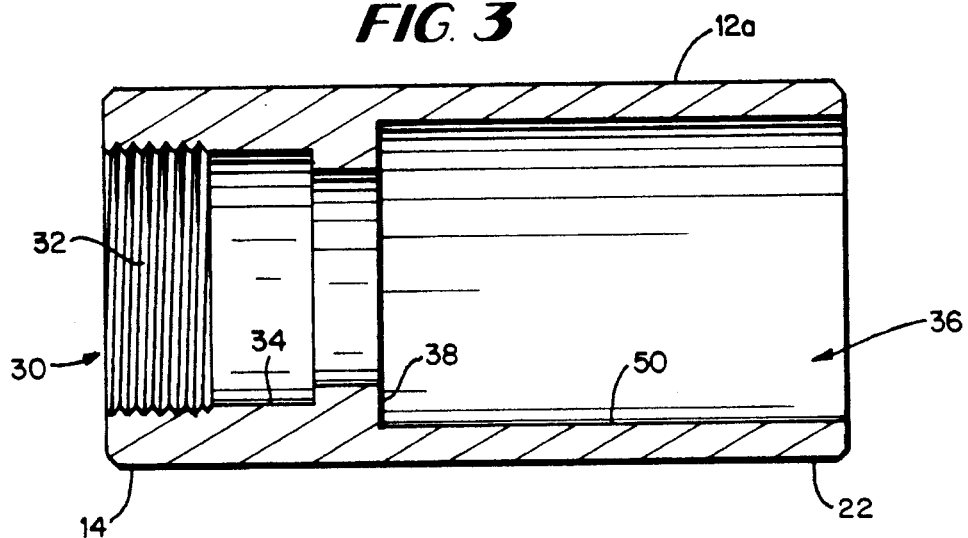
FIG. 3 is a side section of a first section of the housing of the actuator illustrated in FIGS. 1 and 2.

As best seen in FIG. 3, the first housing section 12a is formed at end 14 with a relatively smaller diameter internal bore 30 which includes a threaded portion 32 and a smooth portion 34. The other end 22 of the housing section 12a is formed with a relatively larger diameter, smooth bore 36 which terminates at a radially inwardly directed, annular flange 38 separating the smaller bore 30 from the larger bore 36.

Figure 6:
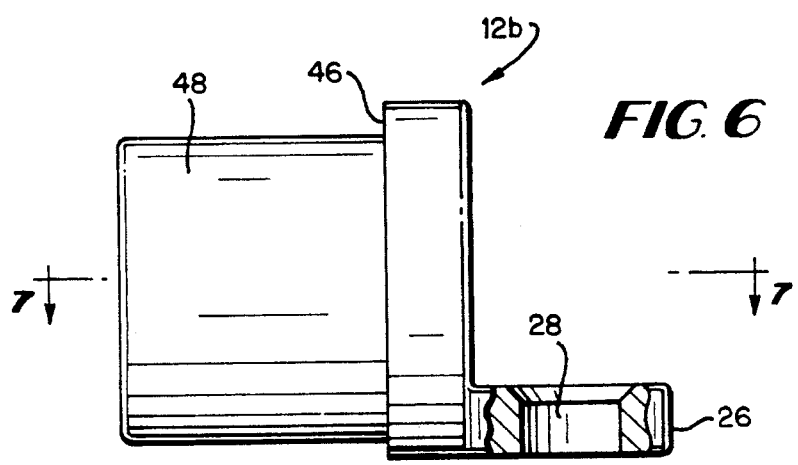
FIG. 6 is a side elevation, partly in section, of a second section of the housing of the device illustrated in FIGS. 1 and 2.
Figure 7:
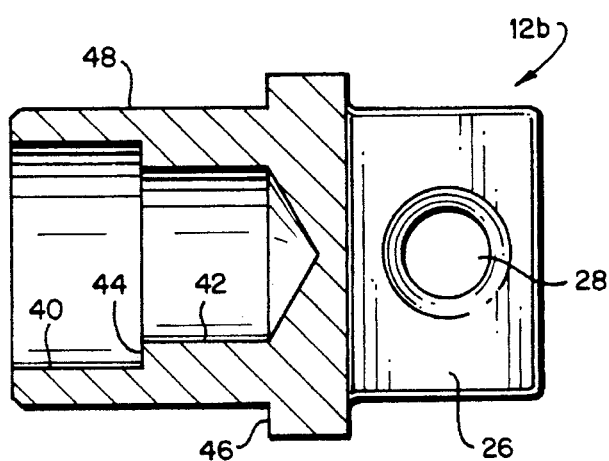
FIG. 7 is a side elevation, partly in section, of the device illustrated in FIG. 6 but rotated 90°.

With reference to FIGS. 6 and 7, the second housing section, or expander sleeve 12b, is counterbored to include relatively larger and smaller internal diameter portions 40 and 42, respectively, as defined by shoulder 44. The exterior of the section 12b is provided with a radial flange 46 which is adapted to engage the edge of housing section 12a when the device 10 is in its fully retracted position as illustrated in FIG. 1. The generally cylindrical exterior surface 48 of the housing section 12b is sized to slidably engage the smooth interior surface 50 of the first housing section 12a.

Figure 8:
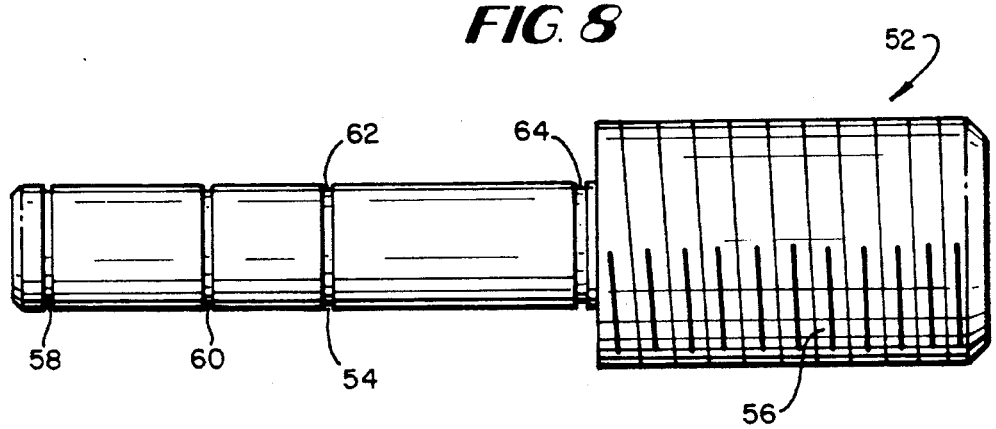
FIG. 8 is a side elevation of the main drive screw in accordance with the invention.

The actuator 10 also includes a main drive screw 52, best seen in FIG. 8, operatively connected between the above described housing sections 12a and 12b. The screw 52 includes a relatively small diameter smooth shaft portion 54 and an enlarged diameter, externally threaded portion 56. The smooth shaft portion 32 is formed with four annular locator grooves 58, 60, 62 and 64. These grooves may receive O-rings or retainer rings during assembly of the variously described components to assist in locating and retaining the components in the desired axial portion. For portion 54, a modified square thread (with eight threads/inch) has been selected because of its very low drag and self-locking ability. It is also relatively easy to produce. With the above screw thread design, the approximate screw torque and efficiency are determined by the following equations:

$$T = \frac{(Qd)}{2} \cdot \frac{(\cos\alpha\tan\lambda + \mu)}{(\cos\alpha - \mu\tan\lambda)};$$

$$\eta = \tan\lambda \frac{\cos\alpha - \mu\tan\lambda}{(\cos\alpha\tan\lambda + \mu)}$$

where in one example, Q=200(N)=44(lb)—the load;

d=⅛–0.0625=0.3125 in.—the mean diameter of the screw;

α=10°/2=5°—one-half the included thread angle;

λ=tan⁻¹(1/πd)—the lead angle;

μ=0.15 —the coefficient of friction.

Returning to FIGS. 1 and 2, and with reference also to FIG. 8 and FIG. 3, the main screw 52 is supported within a thrust bearing 66 press fit within the smooth portion 34 of the housing section 12a, adjacent the plug 16. The bearing 66 abuts the flange 38 and is thus located between the flange 38 and the plug 16, seated on the smooth portion 54 of the bearing between grooves 58 and 60. The main screw 52 is free to rotate within the otherwise fixed bearing, and relative to the first housing section 12a. Since the thrust bearing 66 may be of conventional construction, it need not be described in any further detail here.

Figure 11:
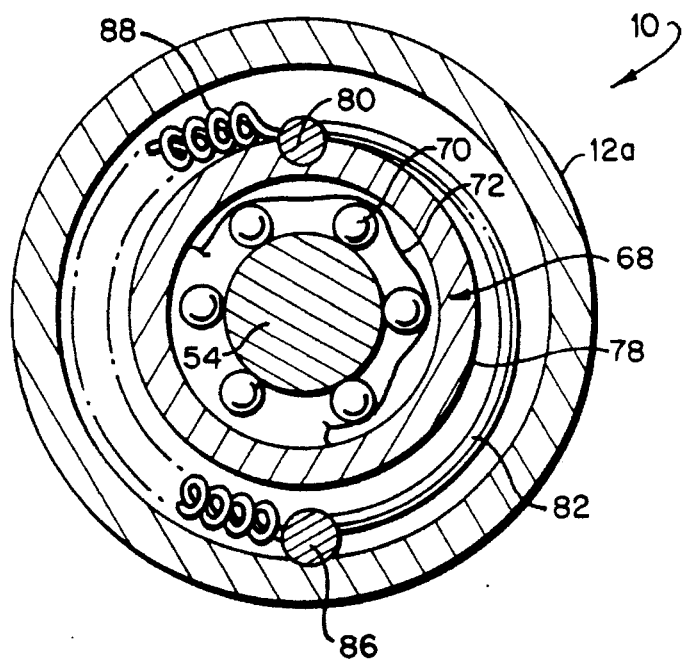
FIG. 11 is a section taken along the line 11—11 of FIG. 1, but showing a clutch mechanism in a simplified form.

A clutch mechanism 68 is also received on the smooth diameter portion 54 of the shaft 52, axially between the grooves 62 and 64. The clutch 68 responds to external stimuli to rotate the main screw in a manner described below. With reference now to FIG. 11, the clutch 68 is preferably a one-way roller-type clutch which includes a series of rollers 70 and associated cams 72 (partially shown) arranged about the reduced diameter, smooth portion 54 of the main screw 52 in the area between grooves 62 and 64. In one direction of rotation, the rollers 70 will be cammed into gripping relationship with the screw shaft portion 54. In an opposite direction of rotation, the cams will release the rollers 70 from the shaft, so that the clutch will freely rotate relative to the shaft. The representation of the clutch as shown in FIG. 11 is simplified to show, in a conceptual way, the functional aspects thereof. This clutch mechanism is known as a "drawn cup" roller clutch and is available from Torrington Inc. as Model No. R C-02.

A nut 76 is press fit within the second housing section 12b and abuts the internal shoulder 44. The nut 76 is formed with an inside surface which is threaded so that the nut may be threaded onto the enlarged threaded portion 56 of the main drive screw 52. With the main screw 52 rotatably journalled in the bearing 66, and with the nut 76 fixed to the second housing section 12b, it will be appreciated that rotation of the axially stationary screw 52 in one direction will cause nut 76 and housing section 12b to move linearly or axially out of the housing section 12a as shown in FIG. 2 to thereby axially lengthen the device 10. Conversely (and in the absence of a one-way clutch), rotation of the screw 52 in an opposite direction will cause the nut 76 and housing section 12b to move linearly or axially back into the housing section 12a to the position shown in FIG. 1. It will be appreciated that the nut 76 may be incorporated as an integral part of the housing section 12b if desired.

Figure 9:
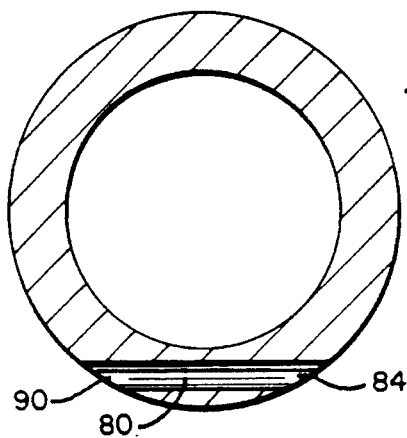
FIG. 9 is a section through a retainer ring for use with the invention.
Figure 10:
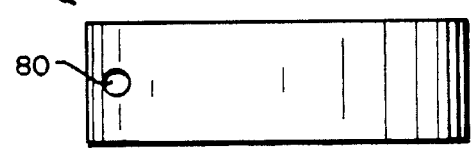
FIG. 10 is a side elevation of the retainer ring of FIG. 9.

A clutch retainer ring 78 (FIGS. 9 and 10) is secured to the external surface of the clutch 68, the ring having a transverse through hole 80 through the thickness of the ring. The clutch retainer ring 78 may have an axial length dimension substantially equal to the axial length of the clutch 68.

It is within the scope of this invention to alter the above described arrangement such that the clutch ring 78, wire 82 and spring 88 be manufactured as a unit, along with the clutch 68.

With reference again to FIGS. 1, 2 and 9–11, a shape memory alloy component 82 is used to actuate the main screw drive shaft 52. A shape memory alloy (for example, Nitinol or other suitable shape memory alloy) restores its shape to a predefined state of strain when heated past an appropriate phase transition temperature. As a result, Nitinol alloys exert large forces as they transform between Martensitic and Austenitic phases. Component 82 is preferably in the form of a Nitinol wire, and has one end secured in an opening 84 of hole 82, as best seen in FIGS. 1 and 11, and conceptually represented in FIG. 11. The other end of the wire 82 is fixed (by any suitable means, e.g., crimping or epoxying) to the interior wall of housing section 12a (conceptually represented at 86 in FIG. 11). At the same time, a coil spring 88 is fixed at one end in an opening 90 of hole 80 with its other end also fixed to the housing at 86 (for example, by spot welding) as best seen in FIG. 11. It will be appreciated that wire component 82 and coil spring 88 may be fixed within the hole 80 simply by crimping the hole, or by any other suitable means.

When the shape memory alloy wire 82 is heated, it contracts to pull the clutch 68 in a clockwise direction as viewed in FIG. 11, causing the rollers 70 to grip portion 54 of the screw shaft 52 and thus turn the drive shaft 52 in the same direction. This, in turn, causes the nut 76 and the housing section 12b to move axially relative to housing section 12a as shown in FIG. 2, and thereby lengthen the device 10. At the same time, spring 88 is extended in the direction of rotation of the clutch 68. When the heat is removed, the shape memory alloy wire 82 softens, allowing the spring 88 to rotate the clutch in an opposite or counter-clockwise direction, back to its original position. Of course, the housing section 126 remains in its extended position because rotation of the clutch in the return direction has no effect on the main screw drive shaft 52.

The manner in which the device is to be heated remotely can vary. For example, ultrasound hypothermia, inductive heating, or an embedded battery powered electric heating mechanism may be employed. One scenario utilizes high energy field waves. For example, with the device 10 fixed between vertebrae or placed on either side of a fractured or shortened long bone, treatment procedures may be carried out utilizing external controls such as radio wave commands and high energy field waves which can penetrate tissue non-destructively. The device will convert the high energy waves to thermal energy which, in turn, will heat the Nitinol wire 82, causing it to retract, i.e., pull the clutch in, for example, a clockwise direction. The treatment may call for between 7 and 10 degrees of rotation in one or more increments. Subsequent treatments at, for example, one or two month intervals, may involve additional rotation in similar increments. The device will thus gradually stretch the spine or long bone (over a period of, for example, six months to a year) with reduced stress not only on the anatomic structures (spine and/or long bones), but on the device attachment points, i.e., bone screws, as well. This will lead to move complete spinal correction, including vertebral rotation and distraction or compression of long bones and/or vertebrae. Of course, the device as disclosed herein is not limited to the treatment of scoliosis, but is equally applicable to skeletal disorders due to accident, illness or other deformity. It can also be applied to limb-lengthening, or any other disorder or deformity where bone segments must be moved relative to each other, in a non-invasive fashion.

It is also within the scope of this invention to include a second clutch on the main drive screw 52 (for example, between grooves 60 and 62), but with the Nitinol wire and return spring oppositely arranged to provide positive linear of the device. It is also to be understood that multiple retraction or axial shortening devices may be employed simultaneously.

Figure 14:
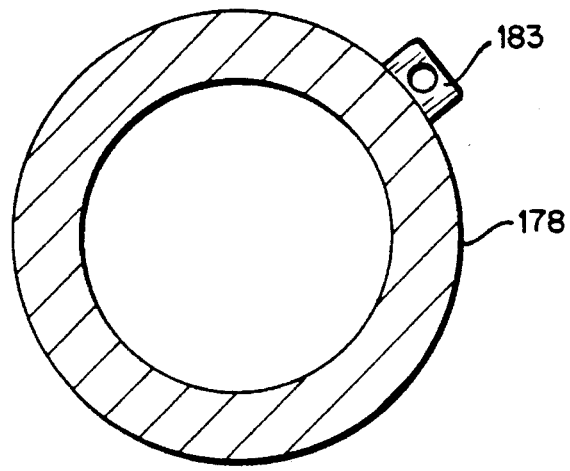
FIG. 14 is a section through the clutch retainer ring utilized in FIGS. 12 and 13.

Turning now to FIGS. 12 and 13, an alternative spring component is provided in the form of a rod spring 188. The latter has a generally J-shape, with a shorter leg 188A secured within a boss or nub 183 (see also FIG. 14) on the ring 178. The shape memory alloy component 182 is also secured at the boss 183 by, for example, wrapping the wire component about the end of the rod spring 182 which passes through the boss 183, and extending the wire back along itself so that both free ends of the wire 182 are secured to the housing as previously described.

A longer leg 188B of the rod spring 188 is secured to the housing 112, again by any suitable means. Transverse portion 188C of the rod spring connects the shorter leg 188A with the longer leg 188B. Note that in the unactuated or unpowered position shown in FIG. 12, legs 188A and B are substantially parallel, with transverse portion 188C extending substantially perpendicularly therebetween.

Actuation (by heating) causes the shape memory alloy wire 182 to contract, pulling the ring 178 in a counterclockwise direction as shown in FIG. 13, causing the clutch 168 to rotate as described above and thus extend the device. Upon cooling, the rod spring 188 returns the clutch 168 and ring 178 to the position shown in FIG. 12. As in the previously described embodiment, the device itself remains in the extended position.

With the exception of the Nitinol wires 82, 182, the components of this device are preferably made of stainless steels because of their resistance to corrosive conditions. Chromium-nickel stainless steel 316 (austenitic) is the most common material currently used for scoliosis devices, and is also eminently suitable for the device disclosed herein. Other biocompatible materials may be considered, however, and coatings which improve biocompatibility may also be considered.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An implantable linear actuator device for use in orthopedic correction procedures, the device comprising:

a housing including a first tubular portion and a second tubular portion, the second tubular portion slidably received in telescoping relationship within the first tubular portion; and a drive mechanism secured within said housing and connected between said first and second tubular portions, said drive mechanism configured and arranged to convert rotational movement to linear movement to thereby extend said second tubular portion in a direction away from said first tubular portion; and externally actuatable shape memory alloy means connected to said drive mechanism for imparting rotational motion to said drive mechanism.

2. The linear actuator of claim 1 wherein attachment tabs are provided on each of said first and second tubular portions.

3. The linear actuator of claim 1 wherein said drive mechanism includes a main screw shaft rotatably journalled at one end in said first tubular portion and threadably connected at an opposite end to said second tubular portion.

4. The linear actuator of claim 3 wherein said drive mechanism further includes a one-way rotatable clutch engageable with said main screw shaft such that rotation of the clutch in one direction will effect rotation of said main screw shaft in said one direction but rotation of the clutch in an opposite direction will not rotate said main screw shaft.

5. The linear actuator of claim 4 wherein said shape memory alloy means includes an elongated wire fixed between said first tubular portion and said clutch.

6. The linear actuator of claim 5 wherein a coil spring is arranged between said clutch and said first tubular member so as to rotate the clutch in said opposite direction upon cooling of said wire.

7. The linear actuator of claim 5 wherein a rod spring is arranged between said clutch and said first tubular member so as to rotate the clutch in said opposite direction upon cooling of said wire.

8. The linear actuator of claim 1 wherein said shape memory alloy means comprises a nickel-titanium alloy wire.

9. An implantable linear actuator device for use in orthopedic correction procedures, the device comprising:

a housing including a first tubular portion and a second tubular portion, the second tubular portion slidably received in telescoping relationship within the first tubular portion; and a drive mechanism secured within said housing and connected between said first and second tubular portions, said drive mechanism including a main screw shaft rotatably journalled at one end in said first tubular portion and threadably connected at an opposite end to said second tubular portion;

a one-way rotatable clutch engageable with said main screw shaft such that rotation of the clutch in one direction will effect rotation of said main screw shaft in said one direction but rotation of the clutch in an opposite direction will not rotate said main screw shaft; and a shape memory alloy component fixed between said clutch and said first tubular portion such that, upon application of heat, said component causes said clutch and said screw shaft to rotate in said one direction.

10. The linear actuator of claim 9 wherein said shape memory alloy component comprises a nickel-titanium alloy wire extending about 180° circumferentially about said clutch.

11. The linear actuator of claim 10 and including a spring fixed between said clutch and said first tubular portion such that, upon removal of heat, said spring component causes said clutch only to rotate in a direction opposite said one direction.

12. The linear actuator of claim 11 wherein said spring comprises a substantially J-shaped rod spring.

13. The linear actuator of claim 11 wherein said spring comprises a coil spring.

* * * * *